(12) United States Patent
Davis

(10) Patent No.: US 7,951,343 B1
(45) Date of Patent: May 31, 2011

(54) TOOTHBRUSH HOLDER AND SANITIZER

(76) Inventor: Annie Davis, Sarasota, FL (US)

( * ) Notice: Subject to any disclaimer, the term of this patent is extended or adjusted under 35 U.S.C. 154(b) by 1170 days.

(21) Appl. No.: 11/517,889

(22) Filed: Sep. 8, 2006

Related U.S. Application Data

(60) Provisional application No. 60/715,200, filed on Sep. 9, 2005.

(51) Int. Cl.
*A61L 2/00* (2006.01)
*A61L 9/00* (2006.01)
*A61L 2/18* (2006.01)
*B01J 19/00* (2006.01)
*B65D 81/24* (2006.01)

(52) U.S. Cl. ............ 422/300; 422/292; 422/28; 422/40; 206/209; 206/209.1

(58) Field of Classification Search .................. 422/300, 422/282, 28, 40; 132/310; 206/362.1, 209, 206/209.01; 49/114, 364; 403/52
See application file for complete search history.

(56) References Cited

U.S. PATENT DOCUMENTS

| 3,904,362 | A | * | 9/1975 | DiPaolo | 206/209.1 |
|---|---|---|---|---|---|
| 3,931,494 | A | * | 1/1976 | Fisher et al. | 219/441 |
| 4,403,484 | A | * | 9/1983 | Fey et al. | 68/23.3 |
| 4,915,219 | A | * | 4/1990 | Ottimo | 206/209.1 |
| D330,979 | S | | 11/1992 | Gruberg | |
| 5,566,823 | A | * | 10/1996 | Summers | 206/209.1 |
| 5,630,505 | A | | 5/1997 | Garcia | |
| 5,725,091 | A | * | 3/1998 | Knoebel | 206/209.1 |
| 5,769,245 | A | | 6/1998 | Butler | |
| 6,009,666 | A | * | 1/2000 | Nakamoto | 49/114 |
| 6,186,324 | B1 | * | 2/2001 | Catterson | 206/362.1 |
| 2003/0168466 | A1 | * | 9/2003 | Spiers et al. | 220/835 |
| 2004/0025899 | A1 | * | 2/2004 | Pinsky | 132/310 |
| 2005/0276736 | A1 | * | 12/2005 | Miller | 422/300 |

FOREIGN PATENT DOCUMENTS

GB 2127680 A * 4/1984

* cited by examiner

*Primary Examiner* — Sean Conley
*Assistant Examiner* — Regina Yoo

(57) ABSTRACT

A toothbrush holder includes an outer body with a bottom section coupled thereto. A seal is intercalated therebetween and extends along the circumference of the outer body. An inner body is seated within the outer body and includes a plurality of chambers equidistantly aligned with a center thereof. The inner body has a diameter less than a diameter of the outer body and has a vertically oriented central shaft formed with the chambers. A top plate is attached to the chambers and is provided with a plurality of apertures counter-sunk therein and vertically aligned above the chambers. A dome-shaped lid is connected to an outer perimeter of the outer body, and disposed adjacent to the top plate. The apparatus includes a mechanism for automatically locking the lid to the outer body after the lid is adapted to a closed position.

15 Claims, 8 Drawing Sheets

TOOTHBRUSH HOLDER AND SANITIZER

CROSS REFERENCE TO RELATED APPLICATIONS

This application claims the benefit of U.S. Provisional Application No. 60/715,200, filed Sep. 9, 2005.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to toothbrush holders and, more particularly, to a toothbrush holder and sanitizer for storing and cleaning toothbrushes when not in use.

2. Prior Art

Toothbrush organizers are desirable for providing a holder to keep toothbrushes free from contamination. Conventional toothbrush holders leave the bristles of the toothbrush unprotected, where they can become contaminated with hairspray, antiperspirants, air fresheners, surface cleaners, splashed soap and water, and other common bathroom contaminants. While many toothbrush holders have been developed to protect the bristles from these outside contaminants, these designs still leave the bristles vulnerable to cross contamination from other toothbrushes stored within the toothbrush holder. The presence of section walls within the cover of the toothbrush organizer isolates the toothbrush heads from one another, thereby making the toothbrushes more sanitary by further reducing opportunities for bristle contamination.

One prior art example shows a holder with a base that includes a central member adapted to rest on a flat horizontal surface. A distal handle end support member for supporting a distal handle end of a toothbrush is configured to rotate relative to the central member. An elongated member extends outward from the distal handle end support member and is fixedly connected to the distal handle end support member. A dome is connected to a distal end of the elongated member and has a completely uncovered open mouth facing the base. A resting member is positioned annularly about the elongated member for leaning the toothbrush there-against near a head of the toothbrush when the distal handle end is supported on the distal handle end support member.

The dome is positioned to cover the head of the toothbrush when the distal handle end is supported on the distal handle end support member and the toothbrush is leaning against the resting member. In another embodiment, the toothbrush holder is configured to hang on a wall. Unfortunately, this example does not provide a means for sterilizing the handle of the toothbrush while stored in the holder. Additionally, this example does not prevent airborne particulates from contacting the bristles of the toothbrush while stored in the holder.

Another prior art example shows a toothbrush organizer with a circular base and a top connected by one or more supports. The top has toothbrush holders adapted to receive electric toothbrushes or manual toothbrushes, along with an optional toothpaste holder for holding toothpaste. Toothbrush receivers are present in the top of the base beneath the toothbrush holders for holding manual toothbrushes. A cover removably encloses the top via a flange that is inserted into a cover receiver. Section walls within the interior of the cover isolate the toothbrush heads from one another. A finger hole in the top of the cover facilitates its removal. Unfortunately, this example also does not provide a means for sterilizing the handle of the toothbrush while stored in the holder.

Accordingly, a need remains for a toothbrush holder and sanitizer to overcome the above-noted shortcomings. The present invention satisfies such a need by providing an apparatus that is simple and easy to use, is lightweight yet durable in design, and provides a convenient multiple toothbrush holder containing a liquid sanitizer. Such a holder provides a convenient storage apparatus that effectively prevents the growth and spreading of germs and bacteria that thrive on and around a toothbrush. The holder effectively reduces the prevalence of colds, flu, infections and gum diseases commonly associated with bathroom germs and bacteria. The holder is compact, easily packable for travel and inexpensive.

BRIEF SUMMARY OF THE INVENTION

In view of the foregoing background, it is therefore an object of the present invention to provide an apparatus for a toothbrush holder and sanitizer. These and other objects, features, and advantages of the invention are provided by a toothbrush holder and sanitizer for storing and cleaning toothbrushes during non-operating conditions.

The apparatus includes an outer cylindrical body including a threadably removable bottom section directly coupled thereto. Such an outer body includes a rubber seal conveniently intercalated between the bottom section and a bottom circumference of the outer body. Such a seal effectively extends along the entire circumference of the outer body. The seal is advantageously situated between the outer body and the bottom section when the bottom section is secured to the outer body such that the seal advantageously prevents premature release of fluids housed within the outer body.

The apparatus further includes an inner cylindrical body rotatably and removably seated within the outer body. Such an inner body conveniently includes a plurality of pie-shaped chambers equidistantly aligned with a center of the inner body. Each of such chambers advantageously has a height equal to a height of the outer body such that the bottom section effectively abuts directly against a bottom end of the chambers during operating conditions. The inner body further has a vertically oriented central shaft monolithically formed with the chambers. The inner body further includes a plurality of divider members radially extending out from a center of the inner body and terminating at an inner perimeter of the inner body such that the chambers are fluidly isolated from the outer body. Such divider members are effectively spaced from the outer body. A ball and socket connection is advantageously intercalated between the bottom section and the inner body such that the inner body freely rotates about the shaft and above the bottom section when seated within the outer body. The inner body conveniently has a diameter less than a diameter of the outer body.

The apparatus preferably further includes a predetermined quantity of sanitizing solution housed within the chambers. Such a sanitizing solution is effectively drained outward from the chambers when the bottom section is detached from the outer body. The apparatus preferably also further contains a plurality of containers detachably interfitted within the chambers. Each of such containers effectively stores a predetermined quantity of the sanitizing solution in isolation from an adjacent one of the containers such that each of the containers advantageously houses a unique species of the sanitizing solution during operating conditions.

The apparatus further includes a top plate directly attached to the shaft such that each one of the chambers and the top plate advantageously rotate in sync along clockwise and counter-clockwise directions. Such a top plate is conveniently provided with a plurality of apertures vertically aligned above the chambers such that a toothbrush is vertically and removably seated within the chambers. Such a plurality of apertures are advantageously counter-sunk within the top plate for effectively directing fluids downwardly therethrough. The top plate has a diameter substantially equal to the diameter of the inner body and is conveniently detachable therefrom.

The apparatus further includes a dome-shaped lid pivotally connected to an outer perimeter of the outer body, and advantageously disposed adjacent to the top plate such that the top plate is effectively inaccessible when the lid is articulated to a closed position. Such a lid is formed from a hardened and transparent material and is concentrically spaced about the top plate.

The apparatus further includes a mechanism for automatically locking the lid to the outer body after the lid is adapted to a closed position. The automatic locking mechanism conveniently includes a locking tab pivotally attached to an outer surface of the outer body and diametrically opposed to a pivot axis of the lid. Such a locking tab is pivotally coupled to an upper edge of the outer body and advantageously extends outwardly therefrom. The locking tab is pivotal about a fulcrum axis tangentially oriented to the circumference of the outer body. A stop member is monolithically formed with an inner surface of the lid and diametrically opposed from the pivot axis. Such a stop member is directly connected to a lower edge of the lid. The stop member is effectively received and captured by the locking tab such that the lid is advantageously prevented from articulating to an open position until a predetermined quantity of downward force is applied to the locking tab. Such a downward force effectively releases the stop member and allows the lid to be biased to an open position for conveniently allowing a user unimpeded access to the toothbrushes held within the inner body.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

Figure 1:
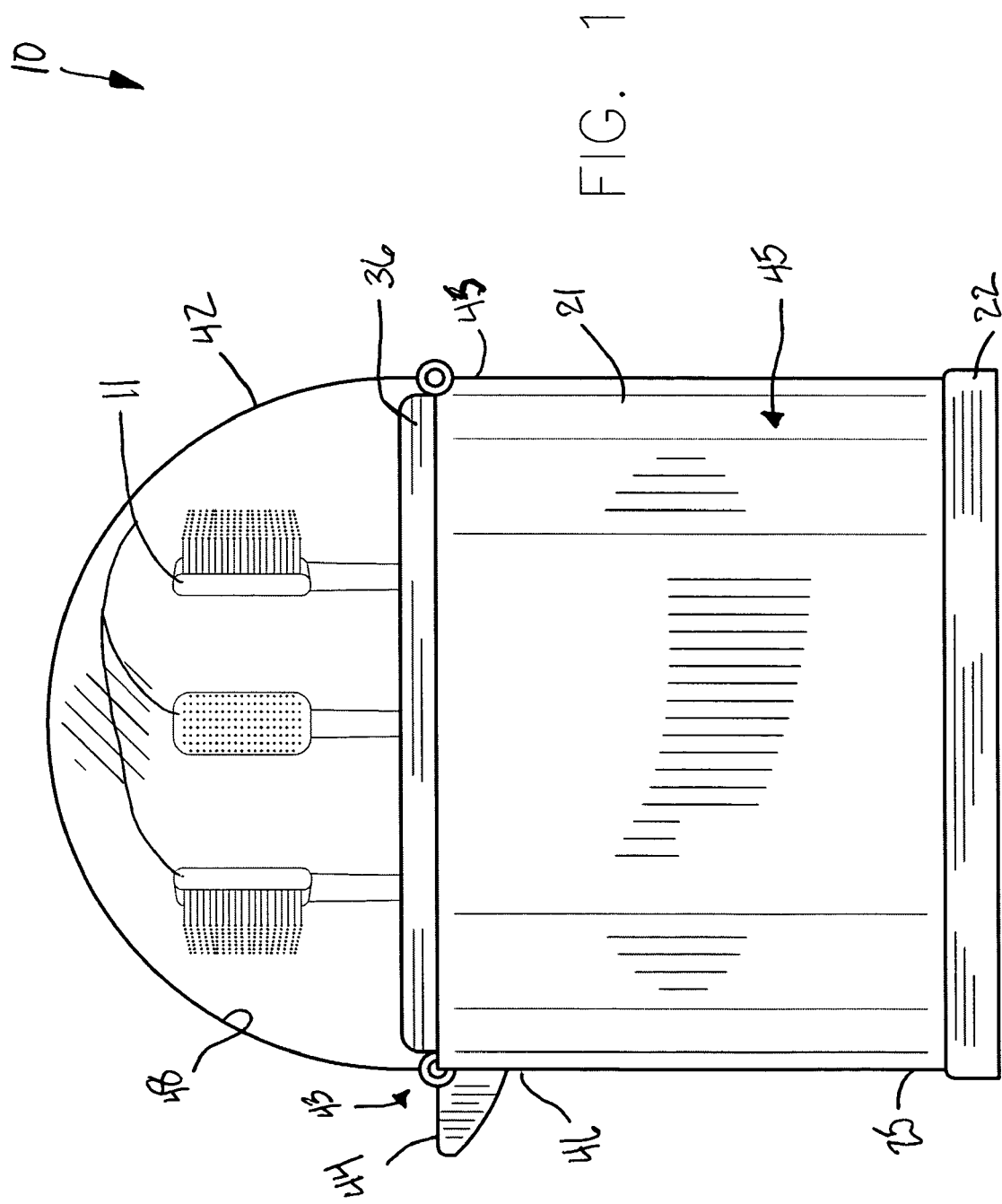
FIG. 1 is a side elevational view of a toothbrush holder and sanitizer, in accordance with the present invention.
Figure 2:
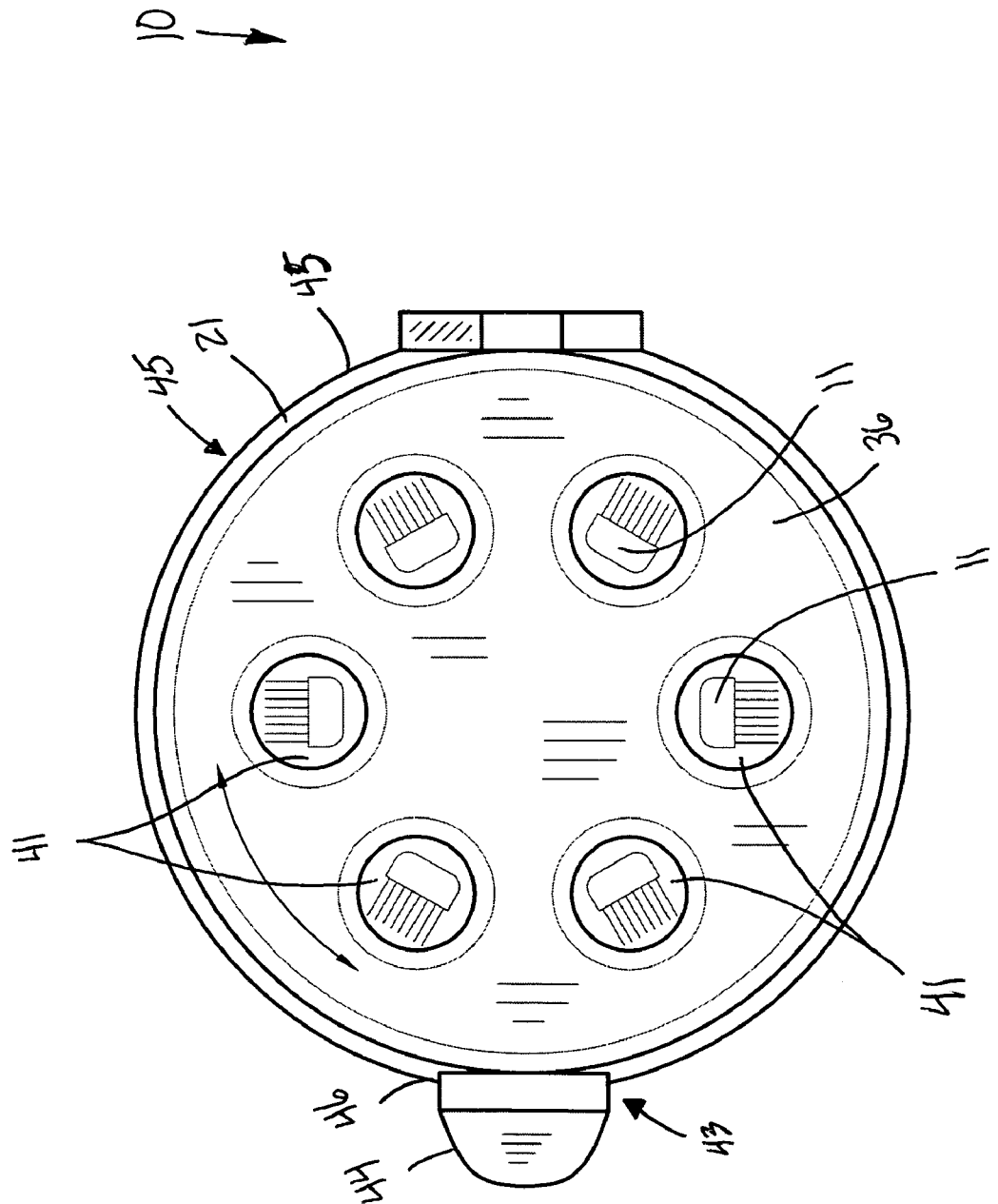
FIG. 2 is a top plan view of the apparatus shown in FIG. 1.
Figure 3:
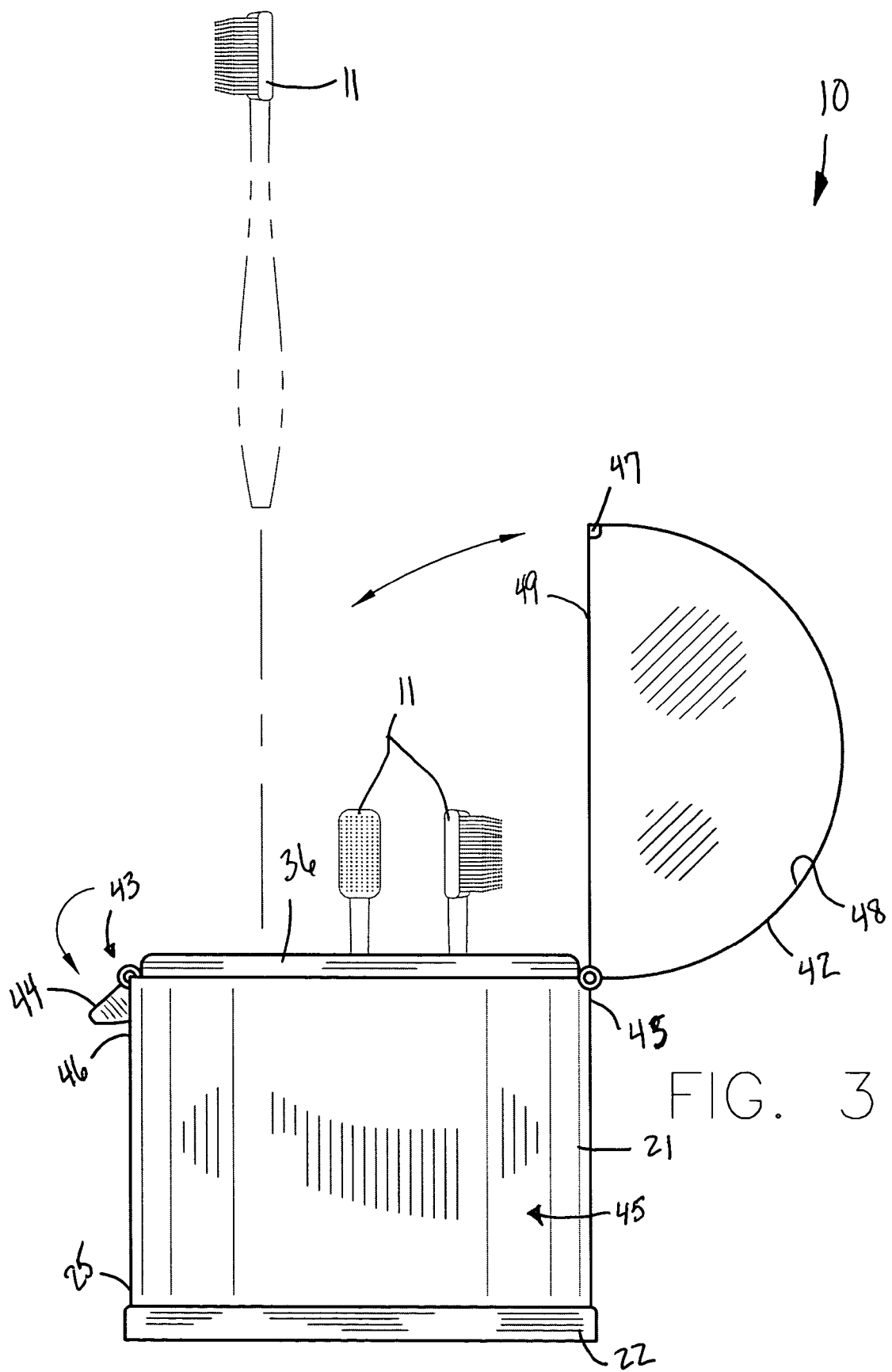
FIG. 3 is a side elevational view of the apparatus shown in FIG. 1 showing the lid biased to an open position.
Figure 4:
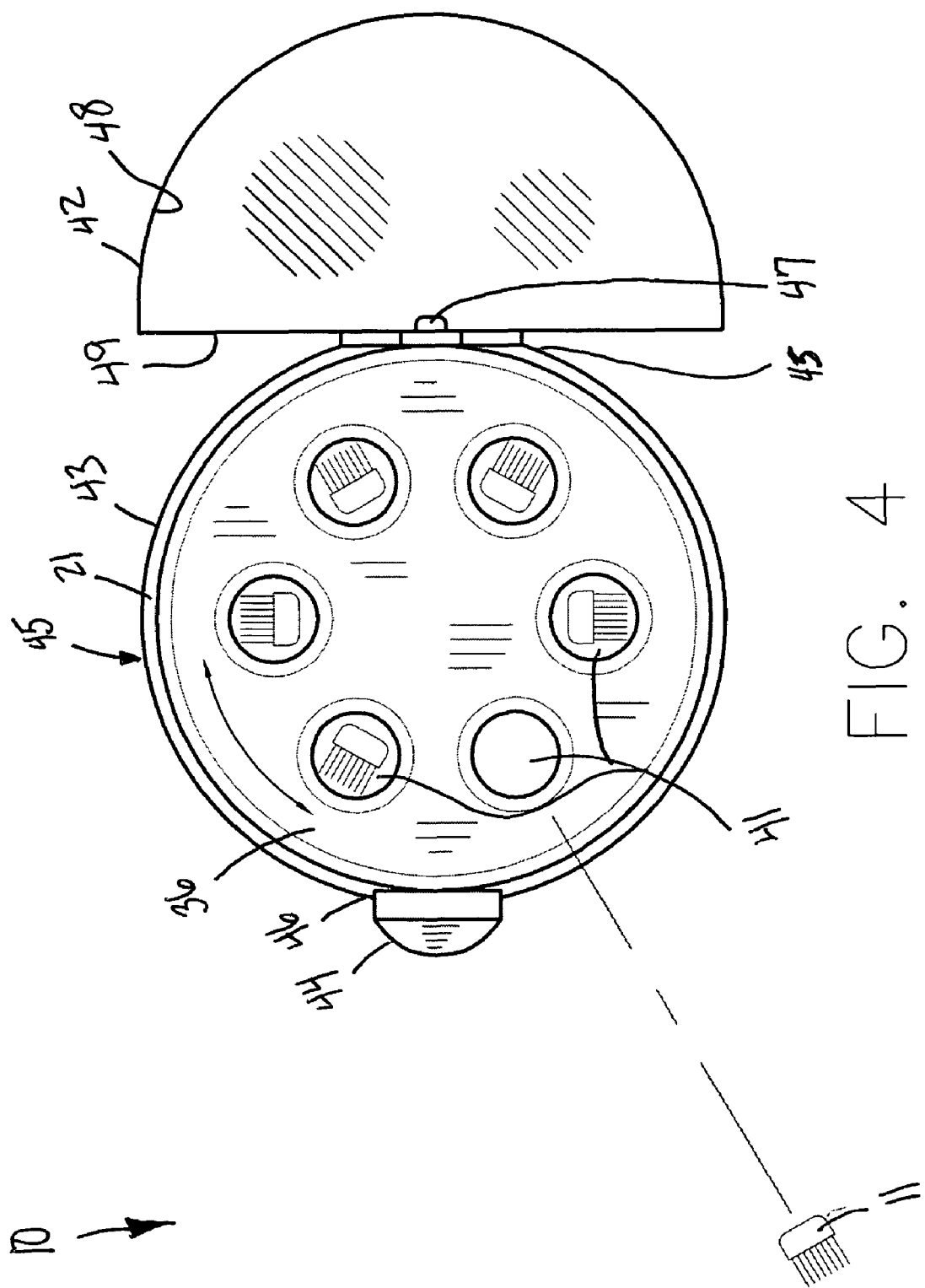
FIG. 4 is a top plan view of the apparatus shown in FIG. 3.
Figure 5:
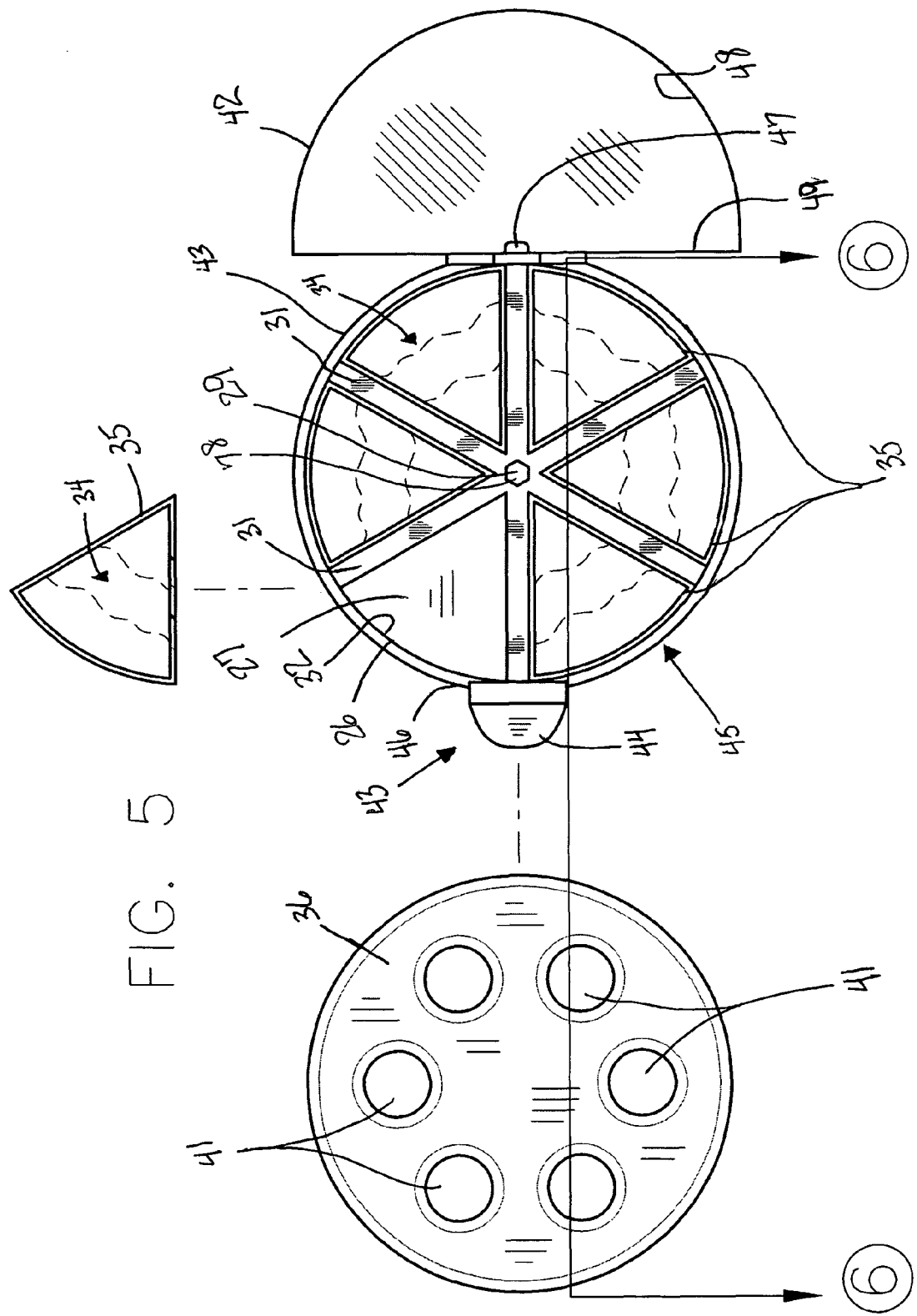
FIG. 5 is a top plan view of the apparatus shown in FIG. 4 showing the top plate detached from the inner body and a container removed therefrom.
Figure 6:
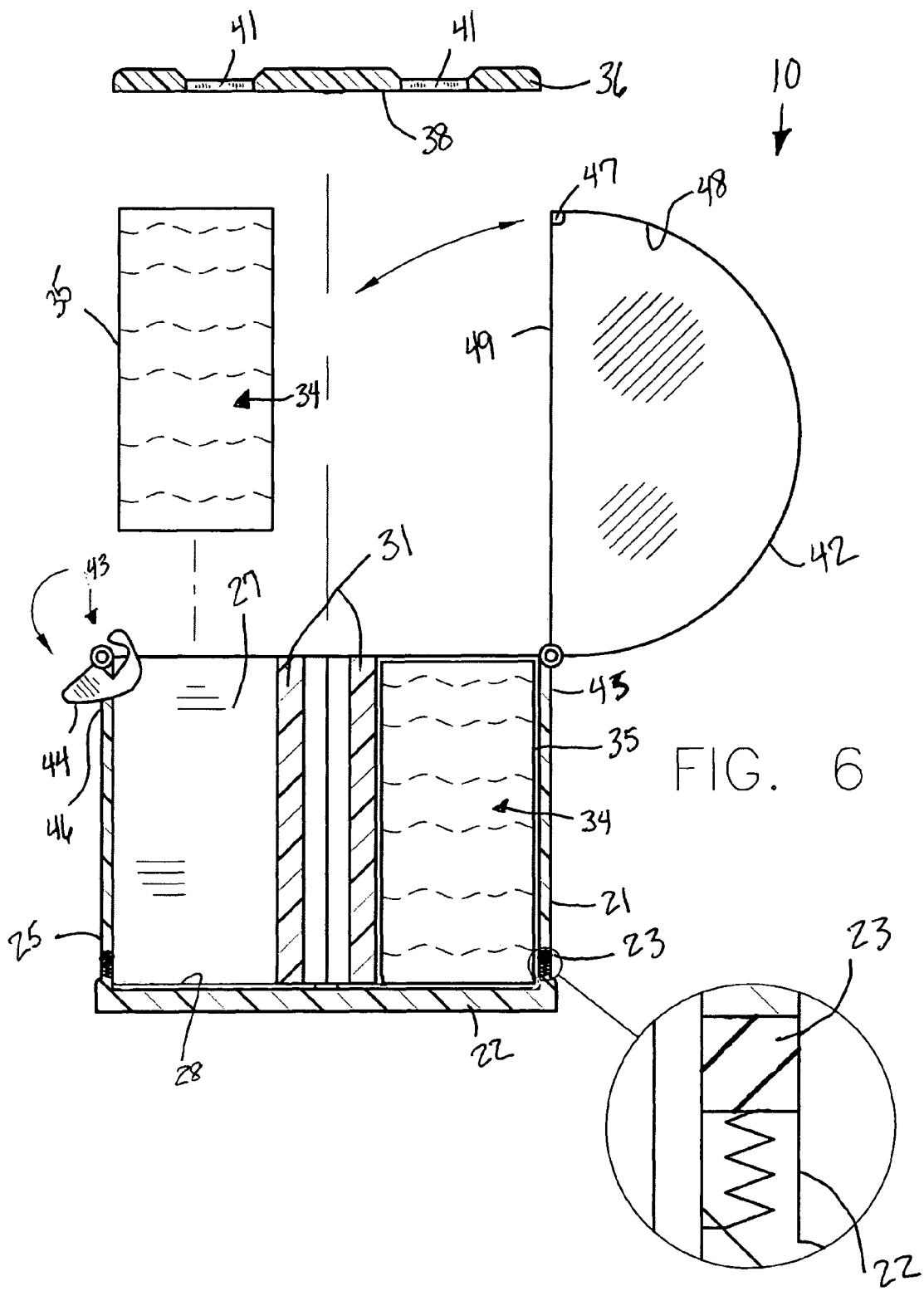
FIG. 6 is a cross-sectional view of the apparatus shown in FIG. 3, taken along line 6-6, showing the top plate detached from the inner body and a container removed therefrom, and an expanded view of the seal.

The apparatus of this invention is referred to generally in FIGS. 1-6 by the reference numeral 10 and is intended to provide a toothbrush holder and sanitizer. It should be understood that the apparatus 10 may be used to hold and sanitize many different types of instruments and should not be limited in use to holding and sanitizing only toothbrushes.

Figure 7:
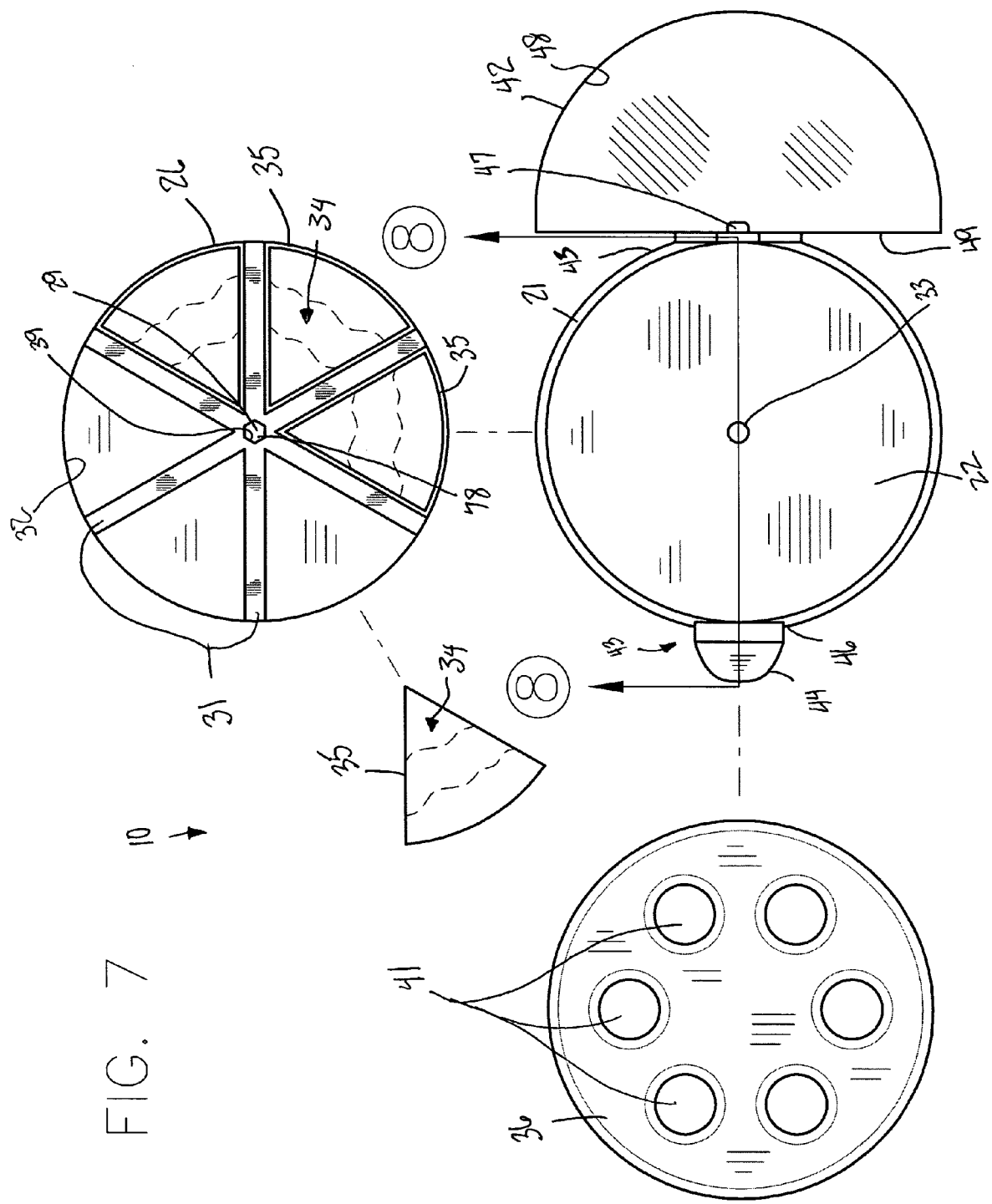
FIG. 7 is a top plan view of the apparatus shown in FIG. 5 showing the inner body removed from the outer body.
Figure 8:
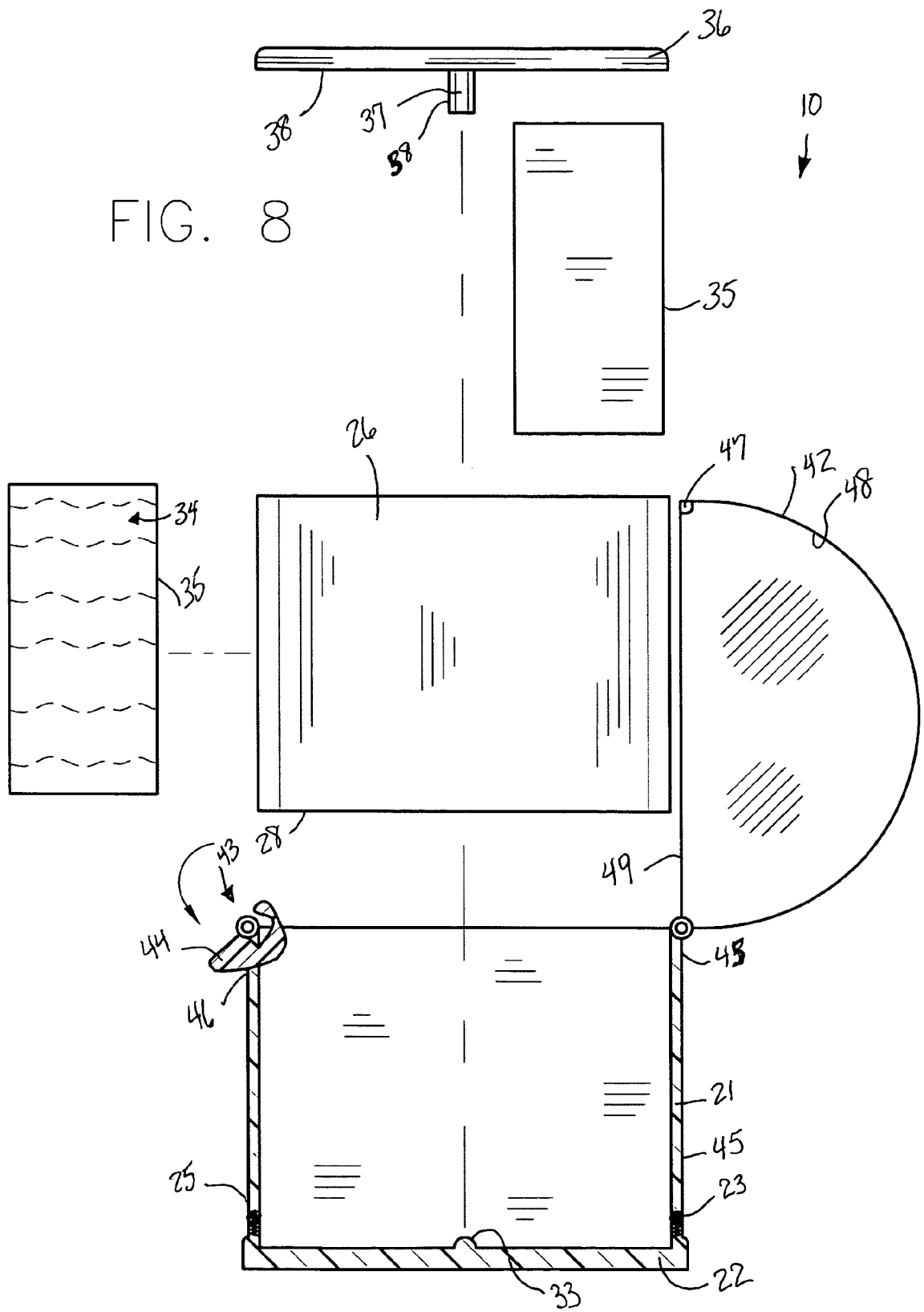
FIG. 8 is side elevational view of the apparatus shown in FIG. 6 showing the inner body removed from the outer body, and showing a cross-sectional view of the outer body only, taken along line 8-8.

Referring initially to FIGS. 1, 2, 3, 4, 5, 6, 7 and 8, the apparatus 10 includes an outer cylindrical body 21 including a threadably removable bottom section 22 directly coupled thereto, without the use of intervening elements. Such an outer body 21 includes a rubber seal 23 conveniently intercalated between the bottom section 22 and a bottom circumference 25 of the outer body 21. Such a seal 23 effectively extends along the entire circumference 25 of the outer body 21. The seal 23 is advantageously situated between the outer body 21 and the bottom section 22 when the bottom section 22 is secured to the outer body 21, which is essential such that the seal 23 advantageously prevents premature release of fluids housed within the outer body 21. Of course, such a seal 23 can be formed from a variety of suitable materials, as is obvious to a person of ordinary skill in the art.

Referring to FIGS. 5, 6, 7 and 8, the apparatus 10 further includes an inner cylindrical body 26 rotatably and removably seated within the outer body 21. Such an inner body 26 conveniently includes a plurality of pie-shaped chambers 27 equidistantly aligned with a center of the inner body 26. Each of such chambers 27 advantageously has a height equal to a height of the outer body 21 such that the bottom section 22 effectively abuts directly against a bottom end 28 of the chambers 27, without the use of intervening elements, during operating conditions. The inner body 26 further has a vertically oriented hollow shaft 29 centrally positioned within the inner body 26 and monolithically formed with the chambers 27. Such a shaft 29 has a hexagonal shaped upper portion 78 and an annular shaped bottom portion. The inner body 26 further includes a plurality of divider members 31 radially extending out from a center of the inner body 26 and terminating at an inner perimeter 32 of the inner body 26, which is vital such that the chambers 27 are fluidly isolated from the outer body 21. Such divider members 31 are effectively spaced from the outer body 21. A ball and socket connection 33 is advantageously intercalated between the bottom section 22 and the inner body 26, which is crucial such that the inner body 26 freely rotates about the shaft 29 and above the bottom section 22 when seated within the outer body 21. The inner body 26 conveniently has a diameter less than a diameter of the outer body 21. Of course, such inner and outer bodies 26, 21 can be produced in a variety of diameters, as is obvious to a person of ordinary skill in the art.

Again referring to FIGS. 5, 6, 7 and 8, the apparatus 10 preferably further includes a predetermined quantity of sanitizing solution 34 housed within the chambers 27. Such a sanitizing solution 34 is effectively drained outward from the chambers 27 when the bottom section 22 is detached from the outer body 21. The apparatus 10 preferably also further contains a plurality of containers 35 detachably interfitted within the chambers 27. Each of such containers 35 effectively stores a predetermined quantity of the sanitizing solution 34 in isolation from an adjacent one of the containers 35, which is critical such that each of the containers 35 advantageously houses a unique species of the sanitizing solution 34 during operating conditions. Of course, such sanitizing solutions 34 can be of many different types, as is obvious to a person of ordinary skill in the art.

Such isolation of the sanitizing solution 34 provides an unexpected benefit of allowing different users to use different types and strengths of sanitizing solutions 34, without contaminating the sanitizing solution 34 of a different user. An adult can effectively use a stronger solution 34 than a child for example. Or, a hypo-allergenic solution 34 may be advantageously used in one container 35 and yet be isolated from other containers 35 during operating conditions, for example. The effective isolation of sanitizing solutions 34 within selected ones of the containers 35 advantageously overcomes prior art shortcomings.

Again referring to FIGS. 1 through 8, the apparatus 10 further includes a top plate 36 directly attached to the shaft 29, without the use of intervening elements, which is vital such that each one of the chambers 27 and the top plate 36 advantageously rotate in sync along clockwise and counter-clockwise directions. Such a top plate 36 has a hexagonal shaped protrusion 37 monolithically formed with a bottom surface 38 of the top plate 36 and extending downwardly from a center thereof. Such a protrusion 37 interfits within the upper portion 78 of the shaft 29 such that an outer surface 58 of the protrusion 37 directly abuts an inner surface 39 of the shaft 29 along an entire circumference of the protrusion 37 during operating conditions. Such a static relationship is critical for ensuring that the top plate 36 and the inner body 26 rotate in sync. The top plate 36 is conveniently provided with a plurality of apertures 41 vertically aligned above the chambers 27 such that a toothbrush 11 is vertically and removably seated within the chambers 27. Such a plurality of apertures 41 are advantageously counter-sunk within the top plate 36, which is essential for effectively directing fluids downwardly therethrough. Of course, such apertures 41 can be formed in a variety of shapes and sizes, as is obvious to a person of ordinary skill in the art. The top plate 36 has a diameter substantially equal to the diameter of the inner body 26 and is conveniently detachable therefrom.

Yet again referring to FIGS. 1 through 8, the apparatus 10 further includes a dome-shaped lid 42 pivotally connected to an outer perimeter 43 of the outer body 21, and advantageously disposed adjacent to the top plate 36, which is essential such that the top plate 36 is effectively inaccessible when the lid 42 is articulated to a closed position. Such a lid 42 is formed from a hardened and transparent material and is concentrically spaced about the top plate 36. Of course, such a lid 42 can be formed from a variety of suitable hardened and transparent materials, as is obvious to a person of ordinary skill in the art.

Yet again referring to FIGS. 1 through 8, the apparatus 10 further includes a mechanism 43 for automatically locking the lid 42 to the outer body 21 after the lid 42 is adapted to a closed position. The automatic locking mechanism 43 conveniently includes a locking tab 44 pivotally attached to an outer surface 45 of the outer body 21 and diametrically opposed to a pivot axis of the lid 42. Such a locking tab 44 is pivotally coupled to an upper edge 46 of the outer body 21 and advantageously extends outwardly therefrom. The locking tab 44 is pivotal about a fulcrum axis tangentially oriented to the circumference 25 of the outer body 21.

Referring to FIGS. 3, 4, 5, 6, 7 and 8, the automatic locking mechanism 43 further includes a stop member 47 is monolithically formed with an inner surface 48 of the lid 42 and diametrically opposed from the pivot axis. Such a stop member 47 is directly connected to a lower edge 49 of the lid 42, without the use of intervening elements. The stop member 47 is effectively received and captured by the locking tab 44, which is critical such that the lid 42 is advantageously prevented from articulating to an open position until a predetermined quantity of downward force is applied to the locking tab 44. Such a downward force effectively releases the stop member 47 and allows the lid 42 to be biased to an open position, which is crucial for conveniently allowing a user unimpeded access to the toothbrushes 11 held within the inner body 26.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A toothbrush holder and sanitizer for storing and cleaning toothbrushes during non-operating conditions, said toothbrush holder and sanitizer comprising:

an outer cylindrical body including a threadably removable bottom section directly coupled thereto;

an inner cylindrical body rotatably and removably seated within said outer body, said inner body further including a plurality of pie-shaped chambers equidistantly aligned with a center of said inner body, each of said chambers having a height equal to a height of said outer body such that said bottom section abuts directly against a bottom end of said chambers during operating conditions, said inner body having a diameter less than a diameter of said outer body, said inner body having a vertically oriented central shaft monolithically formed with said chambers;

a top plate directly attached to said shaft such that each one of said chambers and said top plate rotate in sync along clockwise and counter-clockwise directions, said top plate being provided with a plurality of apertures vertically aligned above said chambers such that a toothbrush is vertically and removably seated within said chambers, wherein said plurality of apertures are counter-sunk within said top plate for directing fluids downwardly therethrough, said top plate having a diameter substantially equal to the diameter of said inner body;

a dome-shaped lid pivotally connected to an outer perimeter of said outer body and disposed adjacent to said top plate such that said top plate is inaccessible when said lid is articulated to a closed position, said lid being formed from a hardened and transparent material; and means for automatically locking said lid to said outer body after said lid is adapted to a closed position, said lid being concentrically spaced about said top plate;

a predetermined quantity of sanitizing solution housed within said chambers, said sanitizing solution being drained outward from said chambers when said bottom section is detached from said outer body.

2. The toothbrush holder and sanitizer of claim 1, wherein said inner body further includes a plurality of divider members radially extending out from a center of said inner body and terminating at an inner perimeter of said inner body such that said chambers are fluidly isolated from said outer body, said divider members being spaced from said outer body.

3. The toothbrush holder and sanitizer of claim 1, further comprising:

a plurality of containers detachably interfitted within said chambers, each of said containers storing a predetermined quantity of said sanitizing solution in isolation from an adjacent one of said containers such that each of said containers houses a unique species of said sanitizing solution during operating conditions.

4. The toothbrush holder and sanitizer of claim 1, further comprising:

a ball and socket connection intercalated between said bottom section and said inner body such that said inner body freely rotates about said shaft and above said bottom section when seated within said outer body.

5. The toothbrush holder and sanitizer of claim 1, wherein said automatic locking means comprises:

a locking tab pivotally attached to an outer surface of said outer body and being diametrically opposed to a pivot axis of said lid, said tab being pivotally coupled to an upper edge of said outer body and extending outwardly therefrom, said tab being pivotal about a fulcrum axis tangentially oriented to a circumference of said outer body; and a stop member diametrically opposed from said pivot axis, said stop member being directly connected to a lower edge of said lid, said stop member being received and captured by said tab such that said lid is prevented from articulating to an open position until a predetermined quantity of downward force is applied to said tab, said downward force releasing said stop member and allowing said lid to be biased to an open position for allowing a user unimpeded access to the toothbrushes held within said inner body.

6. A toothbrush holder and sanitizer for storing and cleaning toothbrushes during non-operating conditions, said toothbrush holder and sanitizer comprising:

an outer cylindrical body including a threadably removable bottom section directly coupled thereto, wherein said outer body further includes a rubber seal intercalated between said bottom section and a bottom circumference of said outer body, said seal extending along the entire circumference of said outer body, said seal being situated between said outer body and said bottom section when said bottom section is secured to said outer body such that said seal prevents premature release of fluids housed within said outer body;

an inner cylindrical body rotatably and removably seated within said outer body, said inner body further including a plurality of pie-shaped chambers equidistantly aligned with a center of said inner body, each of said chambers having a height equal to a height of said outer body such that said bottom section abuts directly against a bottom end of said chambers during operating conditions, said inner body having a diameter less than a diameter of said outer body, said inner body having a vertically oriented central shaft monolithically formed with said chambers;

a top plate directly attached to said shaft such that each one of said chambers and said top plate rotate in sync along clockwise and counter-clockwise directions, said top plate being provided with a plurality of apertures vertically aligned above said chambers such that a toothbrush is vertically and removably seated within said chambers, wherein said plurality of apertures are counter-sunk within said top plate for directing fluids downwardly therethrough, said top plate having a diameter substantially equal to the diameter of said inner body;

a dome-shaped lid pivotally connected to an outer perimeter of said outer body and disposed adjacent to said top plate such that said top plate is inaccessible when said lid is articulated to a closed position, said lid being formed from a hardened and transparent material; and means for automatically locking said lid to said outer body after said lid is adapted to a closed position, said lid being concentrically spaced about said top plate;

a predetermined quantity of sanitizing solution housed within said chambers, said sanitizing solution being drained outward from said chambers when said bottom section is detached from said outer body.

7. The toothbrush holder and sanitizer of claim 6, wherein said inner body further includes a plurality of divider members radially extending out from a center of said inner body and terminating at an inner perimeter of said inner body such that said chambers are fluidly isolated from said outer body, said divider members being spaced from said outer body.

8. The toothbrush holder and sanitizer of claim 6, further comprising:

a plurality of containers detachably interfitted within said chambers, each of said containers storing a predetermined quantity of said sanitizing solution in isolation from an adjacent one of said containers such that each of said containers houses a unique species of said sanitizing solution during operating conditions.

9. The toothbrush holder and sanitizer of claim 6, further comprising:

a ball and socket connection intercalated between said bottom section and said inner body such that said inner body freely rotates about said shaft and above said bottom section when seated within said outer body.

10. The toothbrush holder and sanitizer of claim 6, wherein said automatic locking means comprises:

a locking tab pivotally attached to an outer surface of said outer body and being diametrically opposed to a pivot axis of said lid, said tab being pivotally coupled to an upper edge of said outer body and extending outwardly therefrom, said tab being pivotal about a fulcrum axis tangentially oriented to said circumference of said outer body; and a stop member monolithically formed with an inner surface of said lid and diametrically opposed from said pivot axis, said stop member being directly connected to a lower edge of said lid, said stop member being received and captured by said tab such that said lid is prevented from articulating to an open position until a predetermined quantity of downward force is applied to said tab, said downward force releasing said stop member and allowing said lid to be biased to an open position for allowing a user unimpeded access to the toothbrushes held within said inner body.

11. A toothbrush holder and sanitizer for storing and cleaning toothbrushes during non-operating conditions, said toothbrush holder and sanitizer comprising:

an outer cylindrical body including a threadably removable bottom section directly coupled thereto, wherein said outer body further includes a rubber seal intercalated between said bottom section and a bottom circumference of said outer body, said seal extending along the entire circumference of said outer body, said seal being situated between said outer body and said bottom section when said bottom section is secured to said outer body such that said seal prevents premature release of fluids housed within said outer body;

an inner cylindrical body rotatably and removably seated within said outer body, said inner body further including a plurality of pie-shaped chambers equidistantly aligned with a center of said inner body, each of said chambers having a height equal to a height of said outer body such that said bottom section abuts directly against a bottom end of said chambers during operating conditions, said inner body having a diameter less than a diameter of said outer body, said inner body having a vertically oriented central shaft monolithically formed with said chambers;

a top plate directly attached to said shaft such that each one of said chambers and said top plate rotate in sync along clockwise and counter-clockwise directions, said top plate being provided with a plurality of apertures vertically aligned above said chambers such that a toothbrush is vertically and removably seated within said chambers, wherein said plurality of apertures are counter-sunk within said top plate for directing fluids downwardly therethrough, said top plate having a diameter substantially equal to the diameter of said inner body, wherein said top plate is detachable from said inner body;

a dome-shaped lid pivotally connected to an outer perimeter of said outer body and disposed adjacent to said top plate such that said top plate is inaccessible when said lid is articulated to a closed position, said lid being formed from a hardened and transparent material; and means for automatically locking said lid to said outer body after said lid is adapted to a closed position, said lid being concentrically spaced about said top plate, a predetermined quantity of sanitizing solution housed within said chambers, said sanitizing solution being drained outward from said chambers when said bottom section is detached from said outer body.

12. The toothbrush holder and sanitizer of claim 11, wherein said inner body further includes a plurality of divider members radially extending out from a center of said inner body and terminating at an inner perimeter of said inner body such that said chambers are fluidly isolated from said outer body, said divider members being spaced from said outer body.

13. The toothbrush holder and sanitizer of claim 11, further comprising:

a plurality of containers detachably interfitted within said chambers, each of said containers storing a predetermined quantity of said sanitizing solution in isolation from an adjacent one of said containers such that each of said containers houses a unique species of said sanitizing solution during operating conditions.

14. The toothbrush holder and sanitizer of claim 11, further comprising:

a ball and socket connection intercalated between said bottom section and said inner body such that said inner body freely rotates about said shaft and above said bottom section when seated within said outer body.

15. The toothbrush holder and sanitizer of claim 11, wherein said automatic locking means comprises:

a locking tab pivotally attached to an outer surface of said outer body and being diametrically opposed to a pivot axis of said lid, said tab being pivotally coupled to an upper edge of said outer body and extending outwardly therefrom, said tab being pivotal about a fulcrum axis tangentially oriented to said circumference of said outer body; and a stop member monolithically formed with an inner surface of said lid and diametrically opposed from said pivot axis, said stop member being directly connected to a lower edge of said lid, said stop member being received and captured by said tab such that said lid is prevented from articulating to an open position until a predetermined quantity of downward force is applied to said tab, said downward force releasing said stop member and allowing said lid to be biased to an open position for allowing a user unimpeded access to the toothbrushes held within said inner body.

\* \* \* \* \*